(12) United States Patent
Barbe Garcia et al.

(10) Patent No.: US 8,685,413 B2
(45) Date of Patent: Apr. 1, 2014

(54) **HETEROLOGOUS PROTECTION AGAINST *PASTEURELLA MULTOCIDA* PROVIDED BY *P. MULTOCIDA* FUR CELLS AND THE OUTER-MEMBRANE PROTEIN EXTRACTS THEREOF**

(75) Inventors: Jorge Barbe Garcia, Barcelona (ES); Ignacio Badiola Saiz, Barcelona (ES); Montserrat Llagostera Casas, Barcelona (ES); Maria Elena Garrido Ocana, Barcelona (ES); Montserrat Bosch Gallego, Barcelona (ES); Ana Maria Perez De Rozas Ruiz De Gauna, Barcelona (ES)

(73) Assignee: Universitat Autonoma de Barcelona, Barcelona (ES)

( * ) Notice: Subject to any disclaimer, the term of this patent is extended or adjusted under 35 U.S.C. 154(b) by 504 days.

(21) Appl. No.: 12/865,287

(22) PCT Filed: Jan. 29, 2009

(86) PCT No.: PCT/ES2009/000046
§ 371 (c)(1),
(2), (4) Date: Nov. 22, 2010

(87) PCT Pub. No.: WO2009/095518
PCT Pub. Date: Aug. 6, 2009

(65) Prior Publication Data
US 2011/0104205 A1 May 5, 2011

(30) Foreign Application Priority Data
Jan. 30, 2008 (ES) .................... 200800239

(51) Int. Cl.
| | | |
|---|---|---|
| *A61K 39/02* | (2006.01) | |
| *A61K 39/00* | (2006.01) | |
| *A61K 39/38* | (2006.01) | |
| *A61K 39/102* | (2006.01) | |
| *C12N 1/20* | (2006.01) | |
| *C07K 1/00* | (2006.01) | |
| *C07K 14/00* | (2006.01) | |
| *C07K 17/00* | (2006.01) | |

(52) U.S. Cl.
USPC ................ 424/235.1; 424/184.1; 424/255.1; 424/234.1; 435/252.3; 530/350

(58) Field of Classification Search
None
See application file for complete search history.

(56) References Cited

PUBLICATIONS

Garrido et al., International Microbiology, 2008; 11(1): 17-24.*
Hoppner (Horm Re. 2002, 58 Suppl. 3:7-15).*

* cited by examiner

*Primary Examiner* — Vanessa L Ford
*Assistant Examiner* — Lakia Tongue
(74) *Attorney, Agent, or Firm* — Sughrue Mion, PLLC

(57) ABSTRACT

The invention relates to *Pasteurella multocida* mutants capable of providing heterologous protection against infection caused by virulent *P. multocida*. Said mutants are defective in fur ompH and fur ompH galE genes. The invention relates to *Pasteurella multocida* bacteria vaccine compositions containing fur ompH double mutants and fur ompH galE triple mutants obtained from *P. multocida*, or an extract of iron-regulated outer-membrane proteins (IROMPs) obtained from said mutants, and to an excipient and/or pharmaceutically acceptable adjuvants.

19 Claims, 3 Drawing Sheets

A

B

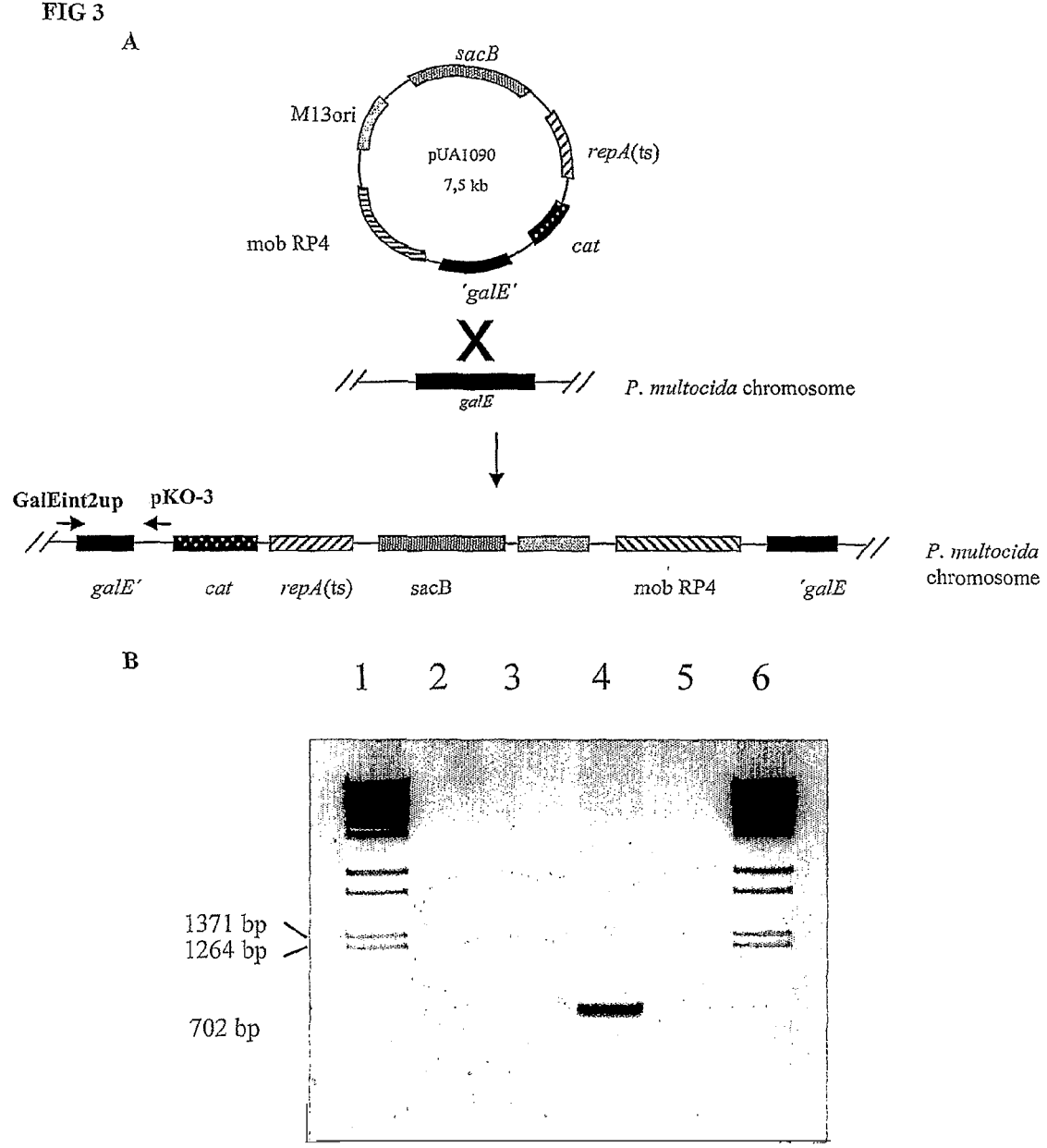

HETEROLOGOUS PROTECTION AGAINST *PASTEURELLA MULTOCIDA* PROVIDED BY *P. MULTOCIDA* FUR CELLS AND THE OUTER-MEMBRANE PROTEIN EXTRACTS THEREOF

FIELD OF THE INVENTION

The invention relates to *Pasteurella multocida* mutants capable of providing heterologous protection against infection caused by virulent *P. multocida*. These mutants are defective in fur ompH and fur ompH galE genes. The present invention relates to vaccine compositions against *Pasteurella* genus bacteria, specifically *Pasteurella multocida*, comprising fur ompH double mutants and fur ompH galE triple mutants, obtained from *P. multocida* or an extract of iron-regulated outer-membrane proteins (IROMPs) obtained from said mutants and an excipient and/or pharmaceutically acceptable adjuvants.

PRIOR STATE OF THE ART

Bacterial infections are a major cause of diseases worldwide both in animals and in humans, especially in children. The *Pasteurella* genus is among the disease-causing bacteria, and it currently includes 20 species, including *Pasteurella multocida*, which is a pathogenic bacterium which causes various infectious diseases such as fowl cholera, bovine pneumonia, hemorrhagic septicemia and atrophic rhinitis in pigs, in animals used for producing foods, so the control of the disease is very important for farmers dedicated to breeding this livestock.

Therefore it is important to develop a vaccine which prevents livestock from being infected. The objective of the development of any vaccine is to provide due protection for the longest time possible.

Essentially three types of vaccines have traditionally been developed: a) "live attenuated vaccines" in which the live pathogen, the virulence of which has been reduced or eliminated, incapacitated for growth, is used, b) vaccines in which purified components of the pathogen are used, and c) "killed vaccines" in which the killed pathogen is used directly. Each of these types of vaccines has its advantages and drawbacks; live attenuated vaccines produce protection under conditions similar to those of the natural disease. However, vaccines of types (b) and (c) are more attractive from the safety point of view.

In veterinary medicine, *P. multocida* vaccination is mainly based on the use of inactivated *P. multocida* cells, known as "bacterins", or in live attenuated bacteria. Bacterins only provide homologous protection; live vaccines provide homologous and heterologous protection, however they contain unknown attenuation markers and, in some cases, have even been associated with epidemic outbreaks.

Patent documents U.S. Pat. Nos. 3,855,408, 4,169,886 and 4,626,430 describe *P. multocida* "live vaccines".

Patent application WO 98/56901 A2, entitled "Live Attenuated Vaccines", describes attenuated bacteria in which the fur gene or a gene homologous thereto, is modified such that the expression of the product of the fur gene, or of its homolog, is regulated independently of the concentration of iron present in the medium in which the bacterium is located. Said bacteria can be used as "live vaccines". The document generally relates to any gram-negative bacterium although it particularly focuses on *Neisseria meningitidis*.

The bacterium is attenuated by mutation of a gene that is essential for producing a metabolite or catabolite not produced by humans or animals. Preferably, the mutations for attenuating the bacterium are in the aro gene or in a gene of the purine or pyrimidine pathway. In another aspect of the invention, the bacterium comprises a recA mutation.

The invention also provides vaccines and the method for producing a bacterium according to the invention and comprising the modification of the native fur gene or of a homolog, of an attenuated bacterium, such that the expression of the fur gene or of its homolog is regulated independently of the concentration of iron present in the environment of the bacterium.

The document indicates that in past attempts to produce live attenuated vaccines, the organisms did not produce certain proteins that are important for cross protection during bulk culture. These proteins included the iron-regulated proteins, the production of which is regulated by the fur gene. Additionally, once these bacteria were administered to the host, the vaccine strains did not have time or metabolic resources during their limited colonization to express these proteins.

The production of attenuated bacteria strains in which the expression of fur has been modified is a technique that can be generally applied. Thus, a pathogenic bacterium the genome of which comprises the fur gene or a homolog thereto, the bacterium being attenuated by suppression or modification of a gene that is essential for the growth in the host in which the bacterium is pathogenic, can be modified as has been described such that the bacterium produces the product of the fur gene or of its homolog independently of the concentration of iron present in the environment of the bacteria. The fur homologs can be identified by comparison with known sequences of other fur genes, such as *E. coli* and *N. meningitidis* for example. Preferably, these homologs are substantially homologous to other known fur genes, with an identity of between 60-70% in a length of at least 100 amino acids. Therefore, genes identified in other bacteria encoding transcription factors and further having the property of responding to the presence of iron, can also be used.

The invention also proposes mutations in recA and comA genes for providing stability to the bacterium used in the vaccine. These mutations must be introduced as final genetic modifications, after the remaining modifications described.

Patent application ES 2 059 503 T3, entitled "*Vacuna contra la pasteurelosis*" (Pasteurollosis Vaccine), describes vaccines against bacteria of the *Pasteurella* genus, and specifically, in certain cases against *Pasteurella multocida*.

The document describes that when the *Pasteurella* organisms are cultured under iron restriction conditions iron, the extraction of the outer membrane or the whole cell lysate generates a protein profile different from the one obtained under normal conditions in vitro, which is more immunogenic than the one produced by the same organism cultured under normal growth conditions. The inactivated *Pasteurella* whole cells cultured under iron restriction conditions which include the "bacterin", for the purpose of preparing a vaccine, are included within the invention.

The invention proposes formulating the vaccine for the use of a homologous serotype, but it also includes a polyvalent vaccine containing iron-regulated proteins of all the pathologically important *Pasteurella* serotypes. Thus, this patent application document is focused on iron-regulated proteins, monoclonal or polyclonal antibodies for said proteins and vaccine formulations in which the protein material can be combined with any of the typical coadjuvants in veterinarian vaccines. The document requires that the proportions of chelating agent to be used must be carefully controlled because too high of a concentration would prevent the culture of the bacteria.

Patent document U.S. Pat. No. 6,790,950 B2, entitled "Anti-bacterial vaccine compositions", identifies gram-negative bacterial virulent genes (focused on *Pasteurella multocida* as a particular case) which allows identifying new antibacterial agents against these virulent genes and their products.

This patent relates to the attempts to produce vaccine compositions traditionally using whole cells of killed (inactivated) bacteria providing only protection specific for a serotype, which involves a problem for the vaccination given the existence of different serotypes. The inventors refer to a study in which an attenuated bacterium vaccine, which produces an inactive form of the toxin ApxII, has shown cross protection.

Taking into account the problems associated with vaccine formulations comprising bacterial strains with undefined, spontaneous mutations, the authors of said document focus on the construction of attenuated bacteria for their use as vaccines that are safe and provide homologous and heterologous protection against *Pasteurella* serotypes, as well as on the identification of attenuated bacteria and genes necessary for the bacterial virulence, which aid in the development of methods for the identification of antibacterial agents. Thus, this document provides gram-negative bacterial organisms (*Pasteurella multocida* among them) containing functional mutations in the sequence of certain genes. This mutation inhibits or prevents the expression or the biological activity of the product encoded by the gene, the effect of this mutation being the attenuation of the bacterial strain virulence.

Compositions comprising mutated and attenuated gram-negative bacterial organisms and, optionally, a pharmaceutically acceptable adjuvant and/or excipient or diluent with a view to the construction of a vaccine which prevents bacterial infection or the symptoms associated with it, are described.

In order for the modified strain of the invention to be effective in a pharmaceutical formulation, the inventors indicate that the attenuation must be significant enough to prevent clinical symptoms of infection, but allowing replication and limited growth of the bacterium in the host.

The invention provide attenuated *P. multocida* strains, vaccines (which can be applied to humans and animals), polynucleotides encoding gene products necessary for the virulence of the gram-negative bacteria, host cells transformed with the polynucleotides of the infection, methods for producing the polypeptides of the invention, methods for the treatment of subjects infected by gram-negative bacteria by means of the administration of the antibacterial agents defined in the invention, etc.

However, this document only claims the polynucleotides encoded by the sequences which are provided as well as the vectors including them and the host cells transformed with them. The mutated *Pasteurella* bacteria described by this invention are used in an attenuated manner.

It should be pointed out that the fur mutation object of the invention of the present application does not imply the reduction of the virulence of the bacterium, so it would not be comprised within this group of mutations. The mentioned document U.S. Pat. No. 6,790,950 B2 refers to the difficulty of providing heterologous protection through vaccination with whole killed cells, which is what the invention of the present application achieves.

Patent application WO 99/29724 A2 entitled "DNA encoding *Pasteurella multocida* outer-membrane protein" claims an isolated and purified nucleic acid molecule comprising a preselected nucleic acid sequence which encodes an avian *Pasteurella multocida* membrane protein or OmpH polypeptide and a biologically active subunit or variant. To that end, they sequence and clone OmpHs of 16 *P. multocida* serotypes (which have an identity of 73%).

This patent application shows studies of homologous protection of chicken through isolated and purified outer-membrane X-73 polypeptides. They also indicate that the immunogenic compositions of the invention can be used in combination with bacterins. These immunogenic compositions comprise an effective amount of isolated and purified *P. multocida* outer-membrane polypeptide in a combination, subunit, peptide, variant or combination of them, together with a pharmaceutically acceptable excipient which, after its administration to vertebrae, induces the production of antibodies specific for *P. multocida* outer-membrane porins. The invention also provides a method for detecting or determining the presence of antibodies which are specific for avian *P. multocida*.

In the article entitled "Use of a reporter gene to follow high-pressure signal transduction in the Deep-Sea Bacterium *Photobacterium* sp. Strain SS9" [Ellen Chi and Douglas H. Bartlett, (American Society for Microbiology, pp. 7533-7540 (1993)], the first genetic system of a barophilic bacterium, *Photobacterium* spl SS9, is developed. The use of this system in the initial characterization of the regulatory mechanisms controlling the expression of the ompH gene in response to changes in hydrostatic pressure is described.

In order to study said relationship between the ompH gene and pressure, an ompHLac *Photobacterium* spl strain is obtained. Mutant ompH strains selected under pressure conditions of 1 atm are also obtained. Four mutants are thus obtained, three of which are not affected in their expression by the pressure of the medium. However, the fourth mutant (EC1002) demonstrates that it is extremely sensitive to pressure. Thus, the future characterization of mutants sensitive to pressure, such as EC1002, will offer the opportunity to identify functions necessary for the adaptation to high pressures.

It is observed that even though in the work described in this article ompH mutants of a gram-negative bacterium are constructed, these mutants are not aimed at immunity studies against said bacterium, furthermore, in this specific case, the defective ompH mutants are aimed at the identification of important functions for growth at high pressures.

Finally, the authors of the present application in the article entitled "Expression of the *Pasteurella multocida* ompH gene is negatively regulated by the Fur protein" [Montserrat Bosch, Raúl Tarragó, M$^a$ Elena Garrido, Susana Campoy, Antonio R. Fernández de Henestrosa, Ana M. Pérez de Rozas, Ignacio Badiola and Jordi Barbé; FEMS Microbiology Letters 203, 35-40 (2001)] delve into the mechanisms and regulation of iron uptake in *P. multocida*. By means of the construction of a *P. multocida* fur mutant, it is demonstrated that the ompH gene, which encodes the main structural membrane protein (which has high antigenicity), is negatively regulated by the Fur protein, iron and glucose. Likewise, it is also demonstrated that wild-type and defective fur *P. multocida* cells have the same level of virulence.

The document explains the role of the fur gene in the iron uptake system of the bacteria through its product, a 17 KDa protein having $Fe^{2+}$-dependent DNA binding activity. The fur protein can act as a positive or negative regulator.

Taking into account that it is known that cultures under iron-deficient conditions induce heterologous protection against infection caused by virulent *P. multocida* strains, the authors propose obtaining, isolating and characterizing a defective fur mutant of this organism. The nucleotide sequence of this gene is registered in GenBank with the Accession Number AF027154.

The article describes the cloning and construction of a *P. multocida* fur mutant. To that end, they inactivate the *P. multocida* fur gene by simple recombination of a suicide plasmid carrying an internal region of the fur gene. By means of PCR amplification and using the Fur1 and Fur2 primers, a fragment of 394 base pairs comprising the 18-412 nucleotides of the fur gene is obtained. This fragment is cloned into the suicide plasmid pUA826, giving rise to the plasmid pUA891 which is introduced in *P. multocida* by "triparental mating". Streptomycin-resistant transconjugants are selected.

The manner of inactivating the fur gene and the amplified region and the primers and plasmids used, are used as the starting point for subsequently obtaining the double and triple mutants, object of the present patent application.

The study carried out in this article subsequently continues analyzing the expression of the wild-type *P. multocida* ompH gene (which encodes the 36 KDa porin indicated above) and in fur mutants. It is observed that the expression of ompH is greater in the fur mutant than in the wild-type strains, which leads to confirming that the expression of ompH is negatively regulated by fur. The work also performs virulence studies of the fur mutant, concluding that both the wild-type *P. multocida* bacteria and the fur mutants have the same level of virulence.

The article concludes that by taking into account that the role of the OmpH protein as an antigen protecting against infection by *P. multocida* for obtaining "bacterins" is demonstrated, the strain to be used must be grown in the absence of glucose due to its inhibitory effect on the expression of the ompH gene.

SUMMARY OF THE INVENTION

An object of the present invention provides materials and methods for producing vaccines comprising *Pasteurella multocida* fur ompH double mutants and fur ompH galE triple mutants, because an outer-membrane protein extract prepared from *Pasteurella multocida* fur ompH mutants provides complete heterologous protection against virulent *Pasteurella multocida*.

The invention also mentions that the use of thermally inactivated *P. multocida* fur ompH mutants and fur ompH galE triple mutants provide 60% cross protection against virulent *P. multocida*. Likewise, the invention points out that when the cells are inactivated by sonication, a higher level of protection is obtained than when they are only treated thermally.

Therefore, an object of the invention is to provide compositions containing said double and triple mutants for being used as immunogenic agents for the protection against virulent *P. multocida*.

Likewise, providing vaccines for preventing infection caused by *P. multocida*, such as pneumonias in pigs, cattle and in small mammals, as well as fowl cholera, is also an object of the invention.

Furthermore, the present invention also provides a kit for administering said vaccine to animals at risk of becoming sick due to *P. multocida*, comprising an outer-membrane protein extract obtained from *P. multocida* defective in fur, fur ompH (double mutant) and/or fur ompH galE (triple mutant) genes and a pharmaceutically acceptable excipient optionally with adjuvants suitable for their subsequent administration.

BRIEF DESCRIPTION OF THE DRAWINGS

FIG. 1A shows the construct of the *P. multocida* fur mutant. Fur3 and Aad3 indicate the positions of the primers used to confirm the presence of the fur mutation.

FIG. 1B shows chromosomal DNA of the wild-type strain (PM1011) (lane 2), fur mutant (PM 1095) (lane 3) and fur ompH mutant (PM1094) (lane 4) that were subjected to PCR analysis with the Aad3 and Fur3 primers (Table 2). The control of PCR without DNA is shown in lane 5. DNA of phage ΦX174 digested with HinfI was used as a molecular weight marker (lanes 1 and 6). PM1094 is deposited in the Colección Española de Cultivos Tipo (CECT), Parc Cientific Universitat de Valencia Catedrático Augustín Escardino, 9 46980 Paterna (Valencia) Spain, with the registration number CECT 8180 and accepted on Oct. 1, 2012, according to the Treaty of Budapest.

FIG. 2A shows the results of the RT-PCR analysis of the transcripts of the ompH1 genes.

FIG. 2B shows the results of the RT-PCR analysis of the transcripts of the ompH2 genes.

FIG. 2C shows the results of the RT-PCR analysis of the transcripts of the genes of the possible ompH1-ompH2 operon.

FIG. 2D shows the results of the RT-PCR analysis of the transcripts of the genes both in the wild-type strain (PM1011) (lane 2) and in the fur ompH mutant (PM1094) (lane 3). Total RNA of each of the strains and the RTompH1up and RTompH1rp, RTompH2up and RTompH2rp and RTompH1up and RTompH2rp primer pairs, respectively, were used. PCRs with wild-type strain DNA (lane 4) and of a negative control without RNA or DNA (lane 5) are also shown. DNA of phages ΦX174 digested with HinfI (B and C) and of phage λ, digested with BstEII (D) were used as molecular weight markers (lanes 1 and 6).

FIG. 3 shows the PCR analysis of the construct of the *P. multocida* galE mutant.

FIG. 3A shows the construct of the *P. multocida* galE mutant. GalEint2up and pKO3-R indicate the positions of the primers used to confirm the presence of the galE mutation.

FIG. 3B shows the chromosomal DNA of the wild-type strain (PM1011) (lane 2), fur ompH mutant (PM1094) (lane 3) and fur ompH galE mutant (PM1096) (lane 4) which were subjected to PCR analysis using the GalEint2up and pKO3-R primers (Table 2). The PCR control without DNA is shown in lane 5. DNA of phage λ digested with BstEII was used as a molecular weight marker (lanes 1 and 6).

DETAILED DESCRIPTION OF THE INVENTION

Figure 1:
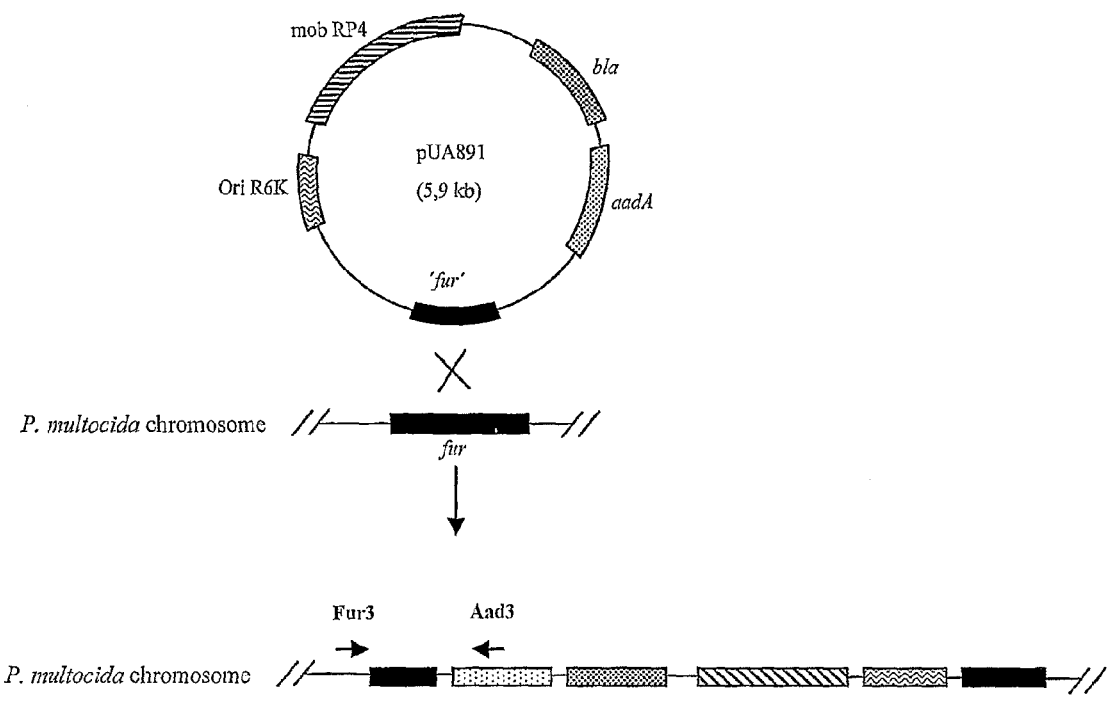
FIG. 1 shows a PCR analysis of the *Pasteurella multocida* fur mutants.
Figure 1:
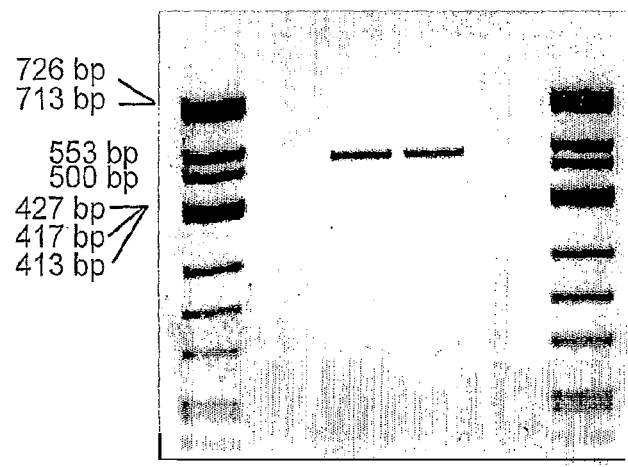

The invention relates to mutants derived from *Pasteurella multocida* capable of promoting heterologous protection against infection caused by *P. multocida* and their use in vaccines. These mutants are defective in the fur gene. This mutant has already been previously described by the same authors of the present application, their use in vaccines not having been described. In addition to *P. multocida* fur, double mutants, such as the fur ompH mutant, and triple mutants, such as the fur ompH galE mutant, are obtained and are also used to provide heterologous protection against infection caused by *P. multocida* by means of their incorporation in vaccines.

Iron is a necessary element for almost all living cells. Many gram-negative pathogenic bacteria, such as *Haemophilus influenzae* and *Neisseria meningitidis*, have in their outer membrane proteins which bind to iron-binding molecules, such as transferrin, lactoferrin, hemoglobin, hemin and ferritin, present in the mucosa of the host organisms (Ratledge, C. and L. G. Dover. Annu. Rev. Microbiol. 54: 881-941. 2000). The expression of almost all these outer-membrane proteins is under the control of the Fur (ferric uptake regulator) protein (Stojiljkovic, I., et al. A. J. Baumler and K. Hantke. J. Mol. Biol. 236: 531-545. J. Mol. Biol. 240: 271. 1994), which binds to the iron present in the cytoplasm of the bacteria. In this reaction, the Fur protein forms a complex with Fe(II), which subsequently binds to a specific DNA sequence, known as "fur box" (2, 12, 14), in the promoter region of iron-regulated genes, thus blocking their transcription. Many iron-regulated outer-membrane proteins (IROMPs) are powerful antigens and factors that are essential for virulence during the infection process of some pathogens (Ratledge, C., and L. G. Dover. Annu. Rev. Microbiol. 54: 881-941. 2000). For this reason, said iron-regulated outer-membrane proteins have been proposed as possible candidates for vaccines based on a purified receptor (Chibber, S., and S. B. Bhardwaj J. Med. Microbiol. 53: 705-706. 2004), or using anti-IROMP antiserum (Sood, S., P. Rishi, V. Dahwan, S. Sharma, and N. K. Ganguly. Mol. Cell. Biochem. 273:69-78. 2005).

*Pasteurella multocida* is a pathogenic bacterium which causes various infectious diseases, such as fowl cholera, bovine pneumonia and hemorrhagic septicemia, and atrophic rhinitis in pigs, in animals used for producing foods. In veterinary medicine, *P. multocida* vaccination is mainly based on using inactivated *P. multocida* cells, known as "bacterins", or in live attenuated bacteria. However, bacterins only provide homologous protection; on the other hand, even though live vaccines provide homologous and heterologous protection, they contain unknown attenuation markers and, in some cases, have even been associated with epidemic outbreaks. The homologous protection has been obtained using *P. multocida* outer-membrane proteins grown without being deprived of iron (Basagoudanavar, S. H., D. K. Singh and B. C. Varshney. J. Vet. Med. 53: 524-530. 2006). Furthermore, several well-defined live attenuated strains which are promising candidates for vaccines have recently been described (10, 17).

Cross protection from bacterins (Glisson, J. R., M. D. Contreras, I. H. Cheng, and C. Wang. Avian. Dis. 37:1074-1079. 1993) as well as from outer-membrane protein extracts (Adler B. et al. J. Biotechnol., Vol. 44, pp. 139-144. 1996; Ruffolo, C. G., et al. B. H. José, and B. Adler. Vet. Microbiol. 59:123-137. 1998) obtained from *P. multocida* grown in iron-deficient medium is known. This heterologous protection seems to be based on the overexpression of *P. multocida* iron-regulated outer-membrane proteins, induced by the absence of iron in the medium, and as a consequence, inside the cells. This approach is limited by the fact that the bacteria grow very poorly in the presence of divalent cation chelating agents, such as 2,2'-dipyridyl (DPD), which is an important limitation for obtaining vaccines in large amounts.

Two hemoglobin binding receptors were initially characterized in *P. multocida* (Bosch, M. et al., M. E. Garrido, M. Llagostera, A. M. Pérez de Rozas. I. Badiola, and J. Barbé. Infect. Immun. 70: 5955-5964. 2002; Cox, A. J., M. L. Hunt, J. D. Boyce, and B. Adler. Microb. Pathog. 34: 287-296, 2003), and it was subsequently demonstrated that this bacteria has at least six hemin and/or hemoglobin binding proteins, all of which are immunogenic (Bosch, M. et al., M. E. Garrido, A. M. Pérez de Rozas, I. Badiola, J. Barbé, and M. Llagostera. Vet. Microbiol. 99: 103-112. 2004); however, when they are inoculated individually, none of them provides protection against a heterologous attack (Bosch, M., M. E. Garrido, M. Llagostera, A. M. Pérez de Rozas, I. Badiola, and J. Barbé. Infect. Immun. 70: 5955-5964. 2002; Bosch, M., M. E. Garrido, A. M. Pérez de Rozas, I. Badiola, J. Barbé, and M. Llagostera. Vet. Microbiol. 99: 103-112. 2004; B. Adler, personal communication).

The recent isolation of the *P. multocida* fur gene has allowed the authors of the present application to construct fur mutants of this bacterial species (Bosch, M., R. Tarragó, M. E. Garrido, S. Campoy, A. R. Fernández de Henestrosa, A. M. Pérez de Rozas, I. Badiola, and J. Barbé. FEMS Microbiol. Lett. 203:35-40. 2001). Given that Fur regulates many bacterial iron uptake proteins, the authors of the present application have studied the heterologous protection provided by *P. multocida* fur cells.

The strategy of using fur mutants solves problems associated with the poor growth which is observed in the culture of bacteria in the presence of iron chelating agents, because the overexpression by the *P. multocida* fur mutant of iron-regulated outer-membrane proteins is similar to the growth of wild-type *P. multocida* cells grown in an iron-deficient medium, preventing the poor growth shown by the cells under these conditions.

The development of vaccines based on iron-regulated outer-membrane proteins, particularly against pathogens having several different iron receptors, as is the case of *P. multocida*, stands out among their uses.

*P. multocida* mutants, all of which are defective in the fur gene, are described as a result of the invention. The fur gene regulates the expression of many iron-regulated proteins in bacteria. Thus, the overexpression of iron-regulated outer-membrane proteins in *P. multocida* fur mutants is similar to the overexpression resulting from the growth of wild-type *P. multocida* cells in iron-deficient medium.

In addition to the fur mutants, fur ompH double mutants are also described, which mutants do not express the OmpH protein (which is highly immunogenic), and the fur ompH galE triple mutants which, in addition to defective in fur and ompH, are also defective in galE.

Together with the mutants of the invention, the oligos used to give rise to the corresponding mutation, the plasmids incorporating them, and the vaccines to which the mutants give rise, are also described. The vaccines can be based on mutant bacteria (containing the previously described mutations) inactivated thermally or by sonication, or based on said iron-regulated outer-membrane proteins to which the *P. multocida* mutants give rise.

Therefore, the present application describes:

a) Mutated *P. multocida* fur gene. This mutation consists of the disruption of the gene by introducing in the bacteria a plasmid containing a fragment of 394 base pairs of the internal region of this gene comprised between nucleotides 18 and 412.

b) The Fur1, Fur2 and Fur3 primers. The Fur1 and Fur2 primers allow cloning by PCR an internal fragment of 394 base pairs of the *P. multocida* fur gene for its subsequent insertion in a plasmid. The Fur3 primer allows checking that the wild-type gene has been interrupted by integrating in *P. multocida* the plasmid integrating the fragment of 394 base pairs of cloned *P. multocida*.

The sequence of the Fur1, Fur2 and Fur3 oligos can be observed in Table 2.

c) Plasmid pUA891, incorporating the streptomycin resistance gene, which is obtained through the suicide plasmid pUA826, and which allows cloning the fragment of 394 base pairs of the *P. multocida* fur gene. This plasmid is introduced in *P. multocida* by triparental mating, subsequently allowing the isolation of the putative fur mutants by selection.

d) Nonsense mutations in the ompH1 and ompH2 genes. Taking into account that in *P. multocida* there are two copies of the ompH gene separated by 154 base pairs, which are independently transcribed, two mutations are described.

The mutation in ompH1 is a nonsense mutation in position 76 which gives rise to a stop codon instead of a glutamine codon, making it express a truncated protein with 24 amino acids. The mutation in ompH2 involves several nucleotide changes, including a nonsense mutation in position 670, which gives rise to a truncated protein with 223 amino acids instead of the 350 which the native protein has. The effect caused by the nonsense mutations in ompH1 and ompH2 is the absence of expression of the 36 KDa OMP protein.

e) OmpH1sequp, OmpH2seqdw, Omp21000, Omp22000, ompH1-2up, RTompH1up, RTompH1rp, RTompH2up and RTompH2dw primers.

The OmpH1sequp and OmpH2seqdw primers amplify the bands containing the *P. multocida* ompH1 and ompH2 genes (Accession number of the ompH1 gene: EF102481 and of the ompH2 gene: EF102482, GenBank) for their subsequent cloning into vectors. Omp21000 and Omp22000 are used to analyze the sequence of the *P. multocida* ompH1 and ompH2 genes. OmpH1-2up is used to analyze the *P. multocida* ompH1 sequence. And RTompH1up, RTompH1rp, RTompH2up, RTompH2dw are used to analyze the transcription of the ompH gene (OmpH1 and OmpH2) in *P. multocida*. The sequence of the indicated oligos can be observed in Table 2.

f) Vectors incorporating the cloned fragment of *P. multocida* using the primers and giving rise, by insertion in *P. multocida*, to the *P. multocida* fur ompH mutant.

g) GalEintup, GalEintrp, GalEint2up, and pKO3-R primers. The GalEintup and GalEintrp primers are those used to obtain the internal fragment of 495 bp of the *P. multocida* galE gene. GalEint2up is a forward primer used to confirm the disruption of the *P. multocida* galE gene. pKO3-R is a primer for confirming the disruption of the *P. multocida* galE gene by insertion of the plasmid pUA891 (plasmid into which the fragment of 495 bp has been cloned) in *P. multocida* fur ompH. The sequences of these primers can be observed in Table 2.

h) Mutant *P. multocida* bacteria. These bacteria are defective in determined genes. The *P. multocida* fur mutants are defective in the fur gene, they prevent the formation of the fur-Fe(II) complex, the blocking of the transcription of iron-regulated genes not occurring. These mutants or the iron-regulated outer-membrane proteins to which they give rise, can be used in the manufacture of *P. multocida* vaccines capable of providing heterologous protection against virulent *P. multocida*. Since the growth in Fe-deficient medium is not necessary, a higher yield in the culture of the bacteria (the growth of which is very poor in the presence of chelating agents) is achieved. The *P. multocida* fur bacteria are obtained after the isolation of the mutants obtained by the insertion of the plasmid incorporating the fragment of 394 base pairs of the *P. multocida* fur gene. Said mutants have already been described (Bosch, M., R. Tarragó, M. E. Garrido, S. Campoy, A. R. Fernández de Henestrosa, A. M. Pérez de Rozas, I. Badiola, and J. Barbé. FEMS Microbiol. Lett. 203:35-40. 2001).

Another object of the invention is constituted by the *P. multocida* fur ompH mutants. Said bacteria are defective in fur and ompH genes. Thus, expression of ompH1 and ompH2 does not occur in them. This means that since said mutants are used in vaccines, they provide greater protection than the fur mutants (an unexpected consequence since ompH encodes the 36 KDa OmpH protein, which is highly immunogenic).

Finally, the *P. multocida* fur ompH galE triple mutants have also been obtained. The objective of the galE mutation is to optimize the surface of exposure of the iron-regulated outer-membrane proteins of the *P. multocida* fur ompH mutant for the purpose of increasing protection against *P. multocida*. To that end, the sequence of the primers used for amplifying a fragment of 495 base pairs of galE, which is subsequently cloned into the plasmid pUA1089, is provided. This plasmid is introduced by triparental mating in *P. multocida* fur ompH PM1094 mutants, the triple mutants subsequently being selected. Nevertheless, the experiments on the effectiveness of these vaccines performed in vivo in mice show a level of protection equal to that provided by the fur ompH mutants.

i) Use of the inactivated *P. multocida* fur, *P. multocida* fur ompH, *P. multocida* fur ompH galE mutant bacteria and/or the iron-regulated outer-membrane proteins thereof, essentially in the form of an extract, in the preparation of a vaccine intended for providing heterologous protection for animals susceptible of being infected by virulent *P. multocida*, said inactivation being thermal or by sonication.

j) Vaccines comprising the *P. multocida* fur, fur ompH or fur ompH galE mutant bacteria, inactivated thermally or by sonication and/or extracts of iron-regulated outer-membrane proteins of these mutants, comprising one or more adjuvants and/or one or more pharmaceutically acceptable excipients. With this application of the invention, i.e., obtaining vaccines, the industrial application requirement for the invention is met.

The studies of protection against *P. multocida* using the double and triple mutants of the present application have been carried out with mice. However, the vaccine can be applied in the control of any of the diseases caused by *P. multocida*, such as pneumonias in pigs and cattle; fowl cholera and pneumonias in small mammals such as rabbits and hamsters, etc.

To formulate the vaccine, the *P. multocida* fur, fur ompH or fur ompH galE mutants can be combined with any of the typical coadjuvants in veterinary vaccines of this type, such as lipopolysaccharides, the Freund's complete or incomplete adjuvant, monophospholipids, such as monophospholipid A, sulfates, phosphates such as aluminum phosphate, and hydroxides such as hydrated aluminum hydroxyphosphate and aluminum hydroxide.

The dose of the vaccine will vary depending on the concentration of the antigenic material; for example, for a vaccine based on inactivated cells, the dose will be 0.1 ml using a concentration of $10^9$ cfu/ml of the fur or fur ompH or fur ompH galE mutant in a solution of 1 ml of physiological saline used as excipient, although the concentration of the active substance will generally be of $7\times10^8$ to $1\times10^9$ cfu/ml in a solution of 1 ml of excipient and optionally an adjuvant, such as 0.7% aluminum hydroxide for example. For a vaccine based on outer-membrane protein extracts, one example would be a dose of 0.1 ml using a concentration of 400 µg of extract in a solution of 1 ml of physiological saline, although the concentration of active substance will generally be of 100 to 400 µg in a solution of 1 ml of excipient and optionally an adjuvant, such as 0.7% aluminum hydroxide for example.

TABLE 1

Bacterial strains and plasmids used in the invention

| Organism and Plasmid | Relevant characteristics | Reference source |
| --- | --- | --- |
| *E. coli* DH5α | F'/supE4 ΔlacU169 (φ80 lacZΔM15) hsdR17 recA1 | Clontech This laboratory |

TABLE 1-continued

Bacterial strains and plasmids used in the invention

| Organism and Plasmid | Relevant characteristics | Reference source |
|---|---|---|
| MC1061 (λpir) | endA1 gyrA96 thi-1 relA1 hsdR mcrB araD139 Δ (araABCleu) 7679 ΔlacX74 gall galK rpsL thi lysogen of the bacteriophage λpir | |
| *P. multocida* | | |
| PM25 | Wild-type, serogroup D | Isolated from rabbit nasal secretion |
| PM108 | Wild-type, serogroup A | Isolated from ovine pneumonia outbreak |
| PM1002 | PM25 Rif$^R$ Spc$^R$ | This laboratory |
| PM1011 | PM108 Rif$^R$ Spc$^R$ | This laboratory |
| PM1094 | PM1011 fur ompH | The present invention |
| PM1095 | PM1011 fur | The present invention |
| PM1096 | PM1094 galE | The present invention |
| Plasmids | | |
| pGEM-T | PCR Ap$^R$ cloning vector | Promega |
| pRK2013 | rep (colEl) Mob$^+$ Tra$^+$ Km$^R$ | (13-Ditta, G., et al. T. Schmidhauser, E. Yakobson, P. Lu, X. W. Liang, D. R. Finlay, D. Guiney, D. R. Helinsky. Plasmid. 13: 149-153. 1985) (18-Link, A. J., et al. D. Phillips, and G. M. Church. J. Bacteriol. 179-6228-6237. 1997) |
| pKO3 | M13ori repA (ts) sacB Cm$^R$ | |
| pUA826 | Mob$^+$ R6K replicon Ap$^R$ Str$^R$ Spc$^R$ | This laboratory |
| pUA1089 | pKO3 containing the mob site of pUA826 | The present invention |
| pUA891 | pUA826 containing an internal fragment of 394 by of the *P. multocida* fur gene | (4-Bosch, M., et al. R. Tarragó, M. E. Garrido, S. Campoy, A. R. Fernández de Henestrosa, A. M. Pérez de Rozas, I. Badiola, and J. Barbé. FEMS Microbiol. Lett. 203: 35-40. 2001) |
| pUA1090 | pUA1089 containing an internal fragment of 495 by of the *P. multocida* galE gene | The present invention |

TABLE 2

Characteristics of the primers used in the present invention

| Primer | Sequence | Position | Application |
|---|---|---|---|
| Fur1 | 5'-AAACTTTTGAAAAAGCGC-3' (SEQ ID NO: 1) | -18[a] | Forward primer for obtaining an internal fragment of 394 by of the *P. multocida* fur gene |
| Fur2 | 5-CTTGACATTACTACATTTGAA-3' (SEQ ID NO: 2) | +412[a] | Reverse primer for obtaining an internal fragment of 394 by of the *P. multocida* fur gene |
| Fur3 | 5-CTTAATAGCAAAATAATTAAGGGGC-3' (SEQ ID NO: 3) | -30[a] | Forward primer used to confirm the disruption of the *P. multocida* fur gene |
| GalEintup | 5'-GTGTTGCTCAAATCACCGGC-3' (SEQ ID NO: 4) | +128[b] | Forward primer for obtaining an internal fragment of 495 by of the *P. multocida* galE gene |
| GalEintrp | 5'-CCACTTGGCTAATATAAGGC-3' (SEQ ID NO: 5) | +622[b] | Reverse primer for obtaining an internal fragment of 495 by of the *P. multocida* galE gene |
| GalEint2up | 5'-AAGCCCTGCCTTCTATGTGG-3' (SEQ ID NO: 6) | -98[b] | Forward primer for confirming the disruption of the *P. multocida* galE gene |
| Aad3 | 5'-GCCCGAGGCATAGACTGTACCCC-3' (SEQ ID NO: 7) | +123[d] | Primer for confirming the disruption of the *P. multocida* fur gene by inserting plasmid pUA891 |
| pK03-R | 5'-TTAATGCGCCGCTACAGGGCG-3' (SEQ ID NO: 8) | 90[d] | Primer for confirming the disruption of the *P. multocida* galE gene by inserting plasmid pUA1090 |
| OmpH1sequp | 5'-CAAACCTATTTTGTTTTGAC-3' (SEQ ID NO: 9) | -161[e] | Forward primer for amplifying the band containing *P. multocida* ompH1 and ompH2 genes PM1011 and PM1094 and analyzing the sequence of the PM1011 and PM1094 *P. multocida* ompH1 gene |
| OmpH2seqdw | 5'-CAAAAACGGTGGTGTCGGTG-3' (SEQ ID NO: 10) | +1228[f] | Reverse primer for amplifying the band containing *P. multocida* ompH1 and ompH2 genes PM1011 and PM1094 and analyzing the sequence of the PM1011 and PM1094 *P. multocida* ompH2 gene |
| Om21000 | CATTTGGGCAAAAGAAGG (SEQ ID NO: 11) | +860[e] | Primer for analyzing the sequence of the PM1011 and PM1094 *P. multocida* ompH2 gene |
| Om22000 | CTGCCACTGCAAAATCTTGG (SEQ ID NO: 12) | +695[f] | Primer for analyzing the sequence of the PM1011 and PM1094 *P. multocida* ompH2 gene |

TABLE 2-continued

Characteristics of the primers used in the present invention

| Primer | Sequence | Position | Application |
|---|---|---|---|
| RTompH1up | CGTTTTAGTAAAGATGTG (SEQ ID NO: 13) | +235[e] | Forward primer for analyzing the transcription of ompH1 in PM1011 and PM109 P. multocida |
| RTompH1rp | GTCACTTTAGATTGTGC (SEQ ID NO: 14) | +779[e] | Reverse primer for analyzing the transcription of ompH1 in PM1011 and PM1094 P. multocida |
| RTompH2up | AAAGAATATTAATAACAACG (SEQ ID NO: 15) | +513[f] | Forward primer for analyzing the transcription of ompH2 in PM1011 and PM1094 P. multocida |
| RTompH2dw | AATCGTACTAACGTCACC (SEQ ID NO: 16) | +735[f] | Reverse primer for analyzing the transcription of ompH2 in PM1011 and PM1094 P. multocida and analyzing the sequence of the ompH2 gene in both strains |
| OmpH1-2up | AATGAGCTGATCGCTAATGC (SEQ ID NO: 17) | +33[f] | Primer for analyzing the sequence of the PM1011 and PM1094 P. multocida ompH1 gene |

[a]Position of the 5' end of the oligonucleotide with respect to the initial transcription point of the P. multocida fur gene
[b]Position of the 5' end of the oligonucleotide with respect to the initial transcription point of the P. multocida galE gene
[c]Position of the 5' end of the oligonucleotide with respect to the initial transcription point of the pUA826 aad gene
[d]Position of the 5' end of the oligonucleotide with respect to the SmaI insertion site in pKO3
[e]Position of the 5' end of the oligonucleotide with respect to the initial transcription point of the P. multocida ompH1 gene
[f]Position of the 5' end of the oligonucleotide with respect to the initial transcription point of the P. multocida ompH2 gene

TABLE 3

Protection provided in mice in the heterologous challenge with PM1002 P. multocida by immunization with outer-membrane proteins

| OMP source strain | Relevant characteristics | Dose[b] (μg/animal) | Survival |
|---|---|---|---|
| PM1011 | Wild-type | 10 | 0/5 |
|  |  | 40 | 0/5 |
| PM1011 | Wild-type grown in the presence of DPD[a] | 10 | 0/5 |
|  |  | 40 | 1/5 |
| PM1095 | fur | 10 | 0/5 |
|  |  | 40 | 1/5 |
| PM1094 | fur ompH | 10 | 4/5 |
|  |  | 40 | 5/5 |
| Control Physiological saline |  |  | 0/5 |

[a]Divalent cation chelating agent 2,2'-dipyridyl
[b]Amount of outer-membrane protein extract inoculated in each animal immunization

TABLE 4

Protection provided in mice in the heterologous challenge with PM1002 P. multocida by means of immunization with inactivated P. multocida strains

| Strain | Inactivation process[a] | Challenge dose (xLD$_{50}$) | Survival |
|---|---|---|---|
| Wild-type | H | 500 | 0/5 |
|  | H | 100 | 0/5 |
| fur oomph | H | 500 | 0/5 |
|  | H | 100 | 3/5 |
| fur oomph galE | H | 500 | 0/5 |
|  | H | 100 | 3/5 |
| Wild-type fur oomph galE | S | 500 | 0/5 |
|  | S | 500 | 3/5 |

TABLE 4-continued

Protection provided in mice in the heterologous challenge with PM1002 P. multocida by means of immunization with inactivated P. multocida strains

| Strain | Inactivation process[a] | Challenge dose (xLD$_{50}$) | Survival |
|---|---|---|---|
| Control Physiological saline |  | 100 | 0/5 |

[a]A suspension of cells at 7 x 10$^8$ cfu/ml was inactivated by heat by means of incubating at 45° C. for 12 h(H) or by sonication (S) and 0.1 ml were inoculated per animal Materials and Methods
Bacterial Strains and Growth Conditions The list of bacterial strains used is shown in Table 1. All the P. multocida strains were grown in liquid medium, in buffered peptone water (BPW) or BHI, in SBA agar plates. When it was necessary, antibiotics were added in the described concentrations (Cárdenas, M. et al. A. R. Fernández de Henestrosa, S. Campoy, A. M. Pérez de Rozas, J. Barbé, I. Badiola, and M. Llagostera. Vet. Microbiol. 80:53-61. 2001). In the growth of the wild-type strain, the concentration of divalent cation chelating agent, 2-2'-dipyridyl DPD (Sigma) used was 150 μM (Table 3).

Genetic Methods

The P. multocida fur mutant was obtained from the plasmid pUA891 (FIG. 1A). This plasmid is obtained as a result of the insertion of an internal fragment of the pUA826 gene (Bosch, M., R. Tarragó, M. E. Garrido, S. Campoy, A. R. Fernández de Henestrosa, A. M. Pérez de Rozas, I. Badiola, and J. Barbé. FEMS Microbiol. Lett. 203: 35-40. 2001) with an internal fragment of the Pasteurella multocida fur gene of 394 bp. pUA826 is derived from pGY2 (26−) from which the cat gene has been extracted by means of restriction with SalI. The plasmid pGY2 has an R6K replication origin (dependent on the λpir protein for replicating, therefore it is suicidal in

*Pasteurella multocida*, it contains the mob mobilization region of RP4 and the genes providing it with resistance to ampicillin (bla), streptomycin and spectinomycin (aadA) and chloramphenicol (cat). This latter gene, as already discussed, is not present in the plasmids pUA826 and pUA891.

The plasmid pUA1090 (FIG. 3A) was used to construct the mutant fur ompH galE. This plasmid is the result of cloning into the plasmid pUA1089 (pKO3 with the mob site of the pUA826) an internal fragment of 495 bp of the *Pasteurella multocida* galE gene. The plasmid pUA1090 was introduced by triparental mating in the fur ompH mutant strain, the transconjugants being selected in selective plates.

To determine the stability of the fur mutation, the fur mutants were sub-cultured 20 consecutive times on SBA plates without adding antibiotics. The concentration of viable bacteria was determined at 5, 15 and 20 passages using suitable dilutions of a suspension of cells ($10^9$ cfu/ml) on SBA plates with and without streptomycin, since pUA891 encodes the gene of resistance to this antibiotic. The stability percentage was calculated as the number of colonies obtained in plates supplemented with antibiotic compared to those which did not contain antibiotic.

It was thus observed that the fur mutation was maintained with 100% stability in cells after 20 passages in the absence of selective pressure.

Biochemical Methods, DNA and RNA Techniques

The methodology and analysis of sequences by computer were carried out as has been described (8-Cárdenas, M., A. R. Fernández de Henestrosa, S. Campoy, A. M. Pérez de Rozas, J. Barbó, I. Badiola, and M. Llagostera. Vet. Microbiol. 80: 53-61. 2001). The primers used are described in Table 2. The nucleotide sequences were determined by the dideoxy method in an ALF Sequencer (Pharmacia Biotech). The RNA extraction and RT-PCR analyses were carried out as has been described (Bosch, M., E. Garrido, M. Llagostera, A. M. Pérez de Rozas, I. Badiola, and J. Barbé. FEMS Microbiol Lett. 210: 201-208. 2002). The *P. multocida* outer-membrane protein extracts were obtained and analyzed as has been described (Bosch, M., E. Garrido, M. Llagostera, A. M. Pérez de Rozas, I. Badiola, and J. Barbé. FEMS Microbiol Lett. 210: 201-208. 2002). The concentrations of protein were measured as has been described (Lowry, O. H., N. J. Rosebrough, A. L. Farr, and R. J. Randall. J. Biol. Chem. 193: 265-275. 1951).

Studies of Protection Against *P. Multocida*

Groups of five Swiss female mice of three weeks of age (Harlan Ibérica; Barcelona, Spain) were intraperitoneally injected with 10 or 40 µg/animal of outer-membrane protein (OMP) extract. The extracts were prepared from different *P. multocida* strains grown in different culture conditions. In all the cases, the volume of inoculated extract was 100 µl which was administered in two doses with two weeks of difference. The control mice were inoculated with 100 µl of physiological saline. The heterologous challenge was carried out three weeks later by intraperitoneal inoculation of 0.1 ml of a virulent *P. multocida* strain (PM1002) which contained 100 or 500 times the $LD_{50}$ thereof.

The same methodology was used for studying the protection provided by the *P. multocida* PM1094 strain (deficient in fur and ompH) and PM1096 strain (deficient in fur, ompH and galE) inactivated thermally or by sonication. The thermal inactivation was achieved by incubation at 45° C. overnight of a culture grown previously in BFn at 30° C. up to a density of $7 \times 10^8$ cfu/ml. The cells inactivated by sonication were prepared by sonicating $7 \times 10^8$ cfu/ml, resuspended in BPW, five times for five minutes in an ice bath at −40° C., with a yield of 80%. The absence of viable cells was tested on SBA plates. In all the cases, the volume of inactivated cell extract inoculated was 100 µl and it was administered in two doses with a two-week interval. The negative control and the heterologous challenge were carried out as has been previously described.

Results

Construction of a *P. multocida* Mutant

The internal fragment of 394-bp of the *P. multocida* fur gene was obtained by PCR amplification using the Fur1 and Fur2 primers (Table 2). The obtained fragment was cloned into the suicide plasmid pUA826, resulting in the plasmid pUA891 (FIG. 1A).

After introducing the plasmid pUA891 in *P. multocida* by triparental mating, several putative fur mutants were isolated after seeding bacteria in suitable selective plates. The analysis of the chromosomal DNA by the PCR technique confirmed that the wild-type fur gene had been interrupted by integration of the plasmid pUA891 (FIG. 1B).

FIG. 1B shows the chromosomal DNA of the wild-type strain (PM1011) (lane 2), fur mutant (PM1095) (lane 3) and fur ompH mutant (PM1094) (lane 4) which were subjected to PCR analysis with the Aad3 and Fur3 primers (Table 2). The PCR control without DNA is shown in lane 5. DNA of phage ΦX174 digested with HinfI was used as a molecular weight marker (lanes 1 and 6).

Likewise, the electrophoretic profiles of the outer-membrane fractions of several fur mutants were analyzed to corroborate that presence of the fur mutation gave rise to the induction of high molecular weight iron-regulated outer-membrane proteins (IROMPs), as has previously been described (4). Two different fur mutant profiles were obtained. Surprisingly, the first mutant expressed the main *P. multocida* 36-KDa outer-membrane protein (OMP), OmpH, while the second one did not.

Figure 2:
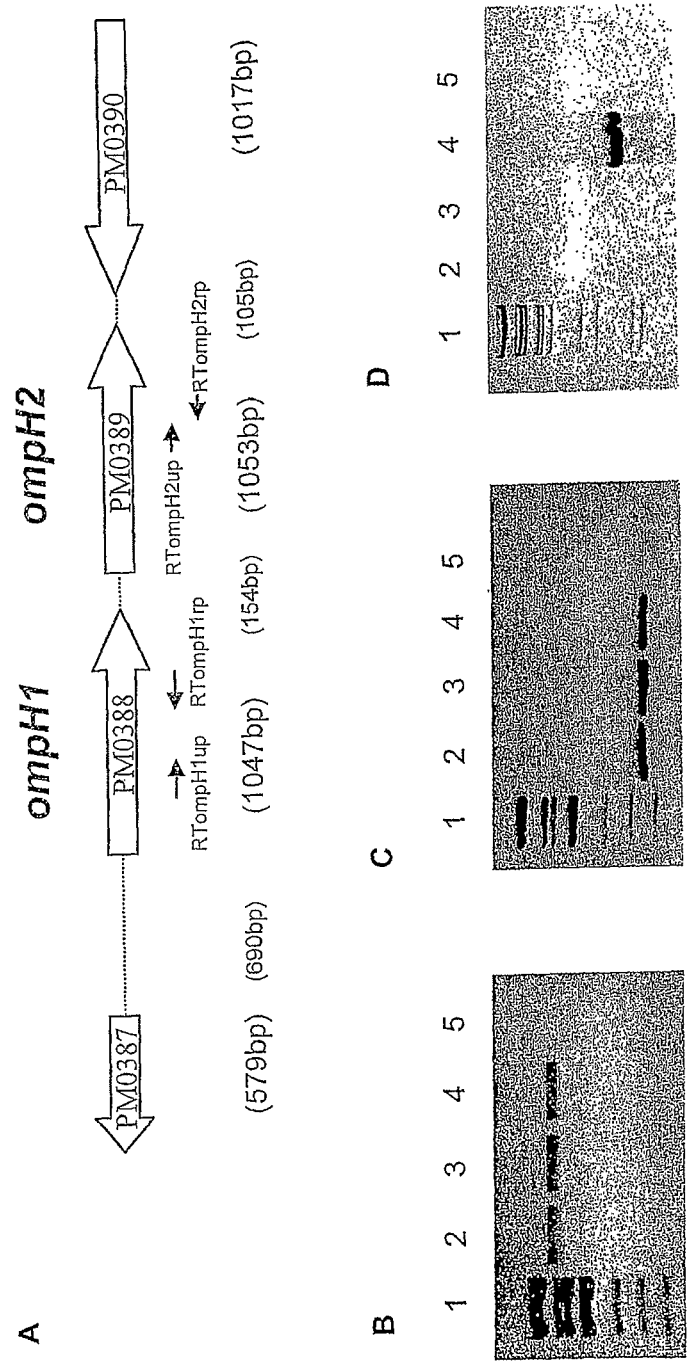
FIG. 2 shows a diagram of the structure of the *P. multocida* ompH1 and ompH2 genes. RTompH1up, RTompH1rp, RTompH2up and RTompH2rp indicate the positions of the primers used for the transcriptional analysis.

In the complete genomic sequence of the *P. multocida*, Pm70 (21), two copies of the ompH gene (separated by 154 bp), encoding the OmpH1 and OmpH2 proteins, were identified. For the purpose of determining the mutation responsible for the phenotype observed in the fur ompH mutant (PM1094 strain), RT-PCR analyses were carried out to determine if the ompH genes had been transcribed. The results demonstrated that ompH1 and ompH2 of the fur ompH mutant had been independently transcribed. However, the DNA sequencing of these genes (GenBank accession number EF102481 and EF102482, respectively) revealed significant differences in comparison with the corresponding sequences of the PM1011 and Pm70 strains. In the ompH1 gene of the fur ompH mutant, a nonsense mutation was found in position 76, giving rise to a stop codon instead of one that encodes glutamine; this gives rise to a very short truncated protein with 24 amino acids. Likewise, the sequence of ompH2 of this mutant had many nucleotide changes, including a nonsense mutation in position 670 which gives rise to a truncated protein with 223 amino acids instead of 350 amino acids. These results clearly indicated that the absence of the main 36-KDa outer-membrane protein (OMP) in the *P. multocida* fur ompH mutant is due to nonsense mutations in ompH1 and ompH2. FIG. 2 shows the diagram of the structure of the *P. multocida* ompH1 and ompH2 genes. RTompH1up, RTompH1rp, RTompH2up and RTompH2rp indicate the positions of the primers used for the transcriptional analysis (A). Sections (B), (C) and (D) show the RT-PCR analysis of the transcripts of the ompH1, ompH2 genes and of the possible ompH1-ompH1 operon both in the wild-type strain (PM1011) (lane 2) and in the fur ompH mutant (PM1094) (lane 3). Total RNA of each of the strains and the RTompH1up and RTompH1rp, RTompH2up and RTompH2rp and RTompH1up and RTompH2rp primer pairs, respectively, were used. PCRs with wild-type strain DNA (lane 4) and of a negative control without RNA or DNA (lane 5) are also shown. DNA of phages ΦX174 digested with HinfI (B and C) and of phage λ, digested with BstEII (D) were used as molecular weight markers (lane 1).

Studies of Protection with *P. Multocida* Fur Mutants

To analyze the putative protective effect of the *P. multocida* fur mutant, groups of five mice were immunized with 10 and 40 μg/animal of outer-membrane protein extract (OMP) prepared from *P. multocida* wild-type PM1011 strain, grown in the absence or presence of DPD, and from the fur and fur ompH mutants. Then the mice were heterologously challenged with the virulent PM1002 strain ($LD_{50}$=3 cfu/animal) with a dose of $500XLD_{50}$. All the mice immunized with outer-membrane protein (OMP) extract obtained from wild-type cells grown in the absence of DPD died two days after the challenge (Table 3). However, the mice immunized with 40 μg of outer-membrane protein (OMP) extract both from the wild-type strain grown in iron-deficient medium and those immunized with the fur mutant showed 20% protection (Table 3). The absence of the main *P. multocida* outer-membrane protein (OMP) in the extract gave rise to complete protection (Table 3) in a significant manner.

Since the highest level of protection was obtained with the outer-membrane protein (OMP) extract prepared from the fur ompH double mutant, the following experiments were focused on the analysis of the protection provided by thermally inactivated cells of this strain. Mice in which a dose of $7\times10^7$ cfu/ml of thermally inactivated fur ompH cells was administered were subsequently subjected to heterologous challenge with a dose of $100XLD_{50}$ of the PM1002 strain; these mice were protected by 60% (Table 4). These results indicate that the simple thermal inactivation of the *P. multocida* fur ompH cells could be used to produce a vaccine providing heterologous protection.

Effect of the galE Mutation in the Protective Capacity of the *P. multocida* Strain For the purpose of determining if the optimization of the surface of exposure of the iron-regulated outer-membrane proteins (IROMPs) increased the protection obtained with inactivated fur ompH cells, a mutation was introduced in the lipopolysaccharide (LPS) of the fur ompH mutant, giving rise to a derivative strain. The product of the galE gene catalyzes the epimerization of UDP-galactose to UDP-glucose and is necessary for the correct synthesis of the center of the lipopolysaccharide. For this purpose, a galE mutant capable of growing in the presence of glucose but incapable of synthesizing surface LPS of the wild-type cells was constructed. By means of PCR amplification with GalEintup and GalEintrp oligonucleotides an internal fragment of the galE gene of 495 bp was obtained. This fragment was cloned into pUA1089 and the resulting plasmid was introduced in the fur ompH strain (PM1094) by triparental mating. After culture in suitable selective plates, several putative galE mutants were obtained.

FIG. 3 describes the PCR analysis of the construct of the *P. multocida* galE mutant. Section (A) shows the construct of the *P. multocida* galE mutant. GalEint2up and pKO3-R indicate the positions of the primers used to confirm the presence of the galE mutation and section (B) shows the chromosomal DNA of the wild-type strain (PM1011) (lane 2), fur ompH mutant (PM1094) (lane 3) and fur ompH galE mutant (PM1096) (lane 4) which were subjected to PCR analysis using the GalEint2up and pKO3-R primers (Table 2). The PCR control without DNA is shown in lane 5. DNA of phage λ digested with BstEII was used as a molecular weight marker (lanes 1 and 6).

The PCR analysis of the chromosomal DNA of four of the transconjugants confirmed that the insertion of pUA1090 interrupted the wild-type galE gene. Then one of these clones, PM1096 (FIG. 3), was chosen for subsequent studies, and the analysis of the outer-membrane protein profile thereof corroborated that it had the same profile as that of the progenitor strain.

Groups of five mice were inoculated with $7\times10^7$ cfu/animal of thermally inactivated fur ompH galE cells (45° C. for 12 hours) and were subsequently faced with the heterologous challenge of PM1002 with doses of 100 and $500xLD_{50}$. As can be seen in Table 4, the animals immunized with the thermally inactivated strain were protected by 60% with the lowest dose. Thus, even though the bacterial cells expressed shorter cell surface LPS, this did not result in an increase of the protection mediated by iron-regulated outer-membrane proteins (IROMPs), because the fur ompH and fur ompH galE mutants induced the same level of protection in mice immunized with any of the strains of these thermally inactivated mutants.

In addition, a different inactivation strategy based on the disruption of cells by sonication was tested. The mice immunized with fur ompH galE cells inactivated by sonication were protected by 60% against the highest dose ($500xLD_{50}$) of virulent bacterium (Table A), these results suggesting that the inactivation of the cells by this method provides a stronger immune response than thermal treatment and that this method of inactivation can therefore be more suitable for the development of vaccines against infection caused by *P. multocida*.

In conclusion, the results submitted show for the first time that the *P. multocida* fur ompH mutant iron-regulated outer-membrane proteins (IROMPs) are immunogenic and provide heterologous protection. Therefore, said results suggest that the fur mutants can be used for the development of vaccines based on iron-regulated outer-membrane proteins (IROMPs), particularly against pathogens having several different iron receptors, as is the case of *P. multocida*. Furthermore, the strategy of using fur mutants solves the problems associated with other methods such as the poor growth the bacterial cells experience in the presence of divalent cation chelating agents.

Literature

1. Adler B., R. Chancellor, P. Homchampa, M. Hunt, C. Ruffolo, R. Strugnell, and D. Wapling. 1996. Immunity and vaccine development in *Pasteurella multocida* infections. J. Biotechnol. 44:139-144.

2. Baichoo, N., and J. D. Helmann. 2002. Recognition of DNA by Fur: a reinterpretation of the Fur box consensus sequence. J. Bacteriol. 184:5826-5832.

3. Basagoudanavar, S. H., D. K. Singh and B. C. Varshney. 2006. Immunization with outer membrane proteins of *Pasteurella multocida* (6:B) provides protection in mice. J. Vet. Med. 53:524-530.

4. Bosch, M., R. Tarragó, M. E. Garrido, S. Campoy, A. R. Fernández de Henestrosa, A. M. Pérez de Rozas, L Badiola, and J. Barbé. 2001. Expression of the *Pasteurella multocida* ompH gene is negatively regulated by the Fur protein. FEMS Microbiol. Lett. 203:35-40.

5. Bosch, M., E. Garrido, M. Llagostera, A. M. Pérez de Rozas, I. Badiola, and J. Barbé. 2002. *Pasteurella multocida* exbB, exbD and tonB genes are physically linked but independently transcribed. FEMS Microbiol Lett. 210:201-208.

6. Bosch, M., M. E. Garrido, M. Llagostera, A. M. Pérez de Rozas, I. Badiola, and J. Barbé. 2002. Characterization of the *Pasteurella multocida* hgbA gene encoding a hemoglobin-binding protein. Infect. Immun. 70:5955-5964.

7. Bosch, M., M. E. Garrido, A. M. Pérez de Rozas, I. Badiola, J. Barbé, and M. Llagostera. 2004. *Pasteurella mul-* tocida contains multiple immunogenic haemin- and haemoglobin-binding proteins. Vet. Microbiol. 99: 103-112.

8. Cárdenas, M., A. R. Fernández de Henestrosa, S. Campoy, A. M. Pérez de Rozas, J. Barbé, I. Badiola, and M. Llagostera. 2001. Virulence of Pasteurella multocida recA mutants. Vet. Microbiol. 80:53-61.

9. Chibber, S., and S. B. Bhardwaj. 2004. Protection in a mouse peritonitis model mediated by iron-regulated outer-membrane protein of Salmonella typhi coupled to its Vi antigen. J. Med. Microbiol. 53:705-709.

10. Chung, J. Y., I. Wilkie, J. D. Boyce, and B. Adler. 2005. Vaccination against fowl cholera with acapsular Pasteurella multocida A:1. Vaccine. 23:2751-2755.

11. Cox, A. J., M. L. Hunt., J. D. Boyce, and B. Adler. 2003. Functional characterization of HgbB, a new hemoglobin binding protein of Pasteurella multocida. Microb. Pathog. 34:287-296.

12. de Lorenzo, V., M. Herrero, F. Giovannini, and J. B. Neilands. 1988. Fur (ferric uptake regulation) protein and CAP (catabolite-activator protein) modulate transcription of fur gene in Escherichia coli. Eur. J. Biochem. 173:537-546.

13. Ditta, G., T. Schmidhauser, E. Yakobson, P. Lu, X. W. Liang, D. R. Finlay, D. Guiney, D. R. Helinski. 1985. Plasmids related to the broad host range vector, pRK290, useful for gene cloning and for monitoring gene expression. Plasmid 13: 149-153.

14. Escolar, L., J. Pérez-Martin, and V. de Lorenzo. 1999. Opening the iron box: transcriptional metalloregulation by the Fur protein. J. Bacteriol. 181:6223-6229.

15. Garrido, M. E., M. Bosch, R. Medina, A. Bigas, M. Llagostera, A. M. Pérez de Rozas, I. Badiola, and J. Barbé. 2003. fur-independent regulation of the Pasteurella multocida hbpA gene encoding a haemin-binding protein. Microbiology 149:2273-2281.

16. Glisson, J. R., M. D. Contreras, I. H. Cheng, and C. Wang. 1993. Cross-protection studies with Pasteurella multocida bacterins prepared from bacteria propagated in iron-depleted medium. Avian. Dis. 37:1074-1079.

17. Hodgson, J. C, A. Finucane, M. P. Dagleish, S. Ataei, R. Parton, and J. G. Coote. 2005. Efficacy of vaccination of calves against hemorrhagic septicemia with a live aroA derivative of Pasteurella multocida B:2 bp two different routes of administration. Infect. Immun. 73:1475-1481.

18. Link, A. J., D. Phillips, and G. M. Church. 1997. Methods for generating precise deletions and insertions in the genome of wild-type Escherichia coli: application to open reading frame characterization. J. Bacteriol. 179:6228-6237.

19. Lowry, O. H., N. J. Rosebrough, A. L. Farr, and R. J. Randall. 1951. Protein measurement with the Folin phenol reagent. J. Biol. Chem. 193:265-275.

20. Luo, Y., J. R. Glisson, M. W. Jackwood, R. E. Hancock, M. Bains, I. H. Cheng, and C. Wang. 1997. Cloning and characterization of the major outer membrane protein gene (ompH) of Pasteurella multocida X-73. J. Bacteriol. 179: 7856-7864.

21. May, B. J., Q. Zhang, L. L. Li, M. L. Paustian, T. S. Whittam, and V. Kapur. 2001. Complete genomic sequence of Pasteurella multocida, Pm70. Proc. Natl. Acad. Sci. USA. 98:3460-3465.

22. Ratledge, C, and L. G. Dover. 2000. Iron metabolism in pathogenic bacteria. Annu. Rev. Microbiol. 54:881-941.

23. Ruffolo, C. G., B. H. Jost, and B. Adler. 1998. Iron-regulated outer membrane proteins of Pasteurella multocida and their role in immunity. Vet. Microbiol. 59:123-137.

24. Sood, S., P. Rishi, V. Dahwan, S. Sharma, and N. K. Ganguly. 2005. Protection mediated by antibodies to iron-regulated outer-membrane proteins of S. thyphi in a mouse peritonitis model. Mol. Cell. Biochem. 273:69-78.

25. Stojiljkovic, L, A. J. Baumler, and K. Hantke. 1994. Fur regulon in gram-negative bacteria. Identification and characterization of new iron-regulated Escherichia coli genes by a Fur titration assay. J. Mol. Biol. 236:531-545. Erratum in: 1994. J. Mol. Biol. 240:271.

26. Young, G. M., Amid, D. and Miller, V. L. 1996. A bifunctional urease enhances survival of pathogenic Yersinia enterocolitica and Morganella morganii at low pH. J. Bacteriol. 178, 6457-6495.

The invention claimed is:

1. A *Pasteurella multocida* (*P. multocida*) mutant strain, comprising a defective fur gene and a defective ompH gene such that expression of fur gene or of ompH1 and ompH2 genes does not occur, wherein the defective fur gene is a wild-type fur gene integrated with an internal nucleotide fragment of 394 base pairs of the wild-type fur gene obtained by amplification with Fur1 (SEQ ID NO: 1) and Fur2 (SEQ ID NO: 2) primers, wherein the defective fur gene is obtained through triparental mating, and the defective OmpH gene has a nonsense mutation at nucleotide position 76 of the oomph1 gene, and a nonsense mutation at nucleotide position 670 of the ompH2 gene.

2. The mutant *P. multocida* bacterium according to claim 1, further comprising a defective galE gene such that a surface of exposure of iron-regulated outer-membrane proteins of the mutant *P. multocida* strain is optimized.

3. The mutated mutant *P. multocida* strain according to claim 1, wherein the nonsense mutation at nucleotide position 76 of the ompH1gene gives rise to a stop codon instead of glutamine resulting in a truncated protein with 24 amino acids, and the nonsense mutation at position 670 of the ompH2 gene gives rise to a truncated protein with 223 amino acids.

4. The mutated mutant *P. multocida* strain according to claim 3, wherein the nonsense mutations in the ompH1 gene and the ompH2 gene results in an absence of an OmpH main 36-KDa outer-membrane protein.

5. The mutant *P. multocida* strain according to claim 2, wherein the defective galE gene is wild-type galE gene integrated with an internal nucleotide fragment of 495 base pairs of the wild-type galE gene obtained by amplification with GalEintup and GalEintp primers.

6. The mutant *P. multocida* strain according to claim 1, wherein the strain is inactivated.

7. The mutant *P. multocida* strain according to claim 6, wherein the strain is inactivated thermally.

8. The mutant *P. multocida* strain according to claim 6, wherein the strain is inactivated by sonication.

9. A preparation of outer-membrane proteins of the mutant *P. multocida* strain according to claim 1.

10. A method for preparing an immunogenic composition comprising:
  a. obtaining a mutant *P. multocida* strain defective in fur and ompH genes such that the expression of fur gene or of ompH1 and ompH2 genes does not occur, or a preparation of outer-membrane proteins thereof;
    wherein the defective fur gene is a wild-type fur gene integrated with an internal nucleotide fragment of 394 base pairs of the wild-type fur gene obtained by amplification with Fur1 (SEQ ID NO: 1) and Fur2 (SEQ ID NO: 2) primers, wherein the defective fur gene is obtained through triparental mating, and the defective OmpH gene has a nonsense mutation at nucleotide position 76 of the ompH1 gene, and a nonsense mutation at nucleotide position 670 of the ompH2 gene;
  b. extracting cells obtained in (a) containing the mutant *P. multocida* strain or the preparation of outer-membrane proteins thereof;
  c. combining the extract of (b) in an effective amount with an excipient and/or pharmaceutically acceptable adjuvants.

11. The method for preparing an immunogenic composition according to claim 10, wherein the mutant *P. multocida* strain is a fur ompH double mutant or a fur ompH galE triple mutant, which has been thermally inactivated.

12. The method for preparing an immunogenic composition according to claim 10, wherein the mutant *P. multocida* strain is a fur ompH double mutant or a the fur ompH gale triple mutant, which has been inactivated by sonication.

13. An immunogenic composition comprising an immunogenic effective amount of the mutant *P. multocida* strain or preparation of outer-membrane proteins thereof according to claim 10, wherein the mutant *P. multocida* strain is a fur ompH double mutant or a fur ompH galE triple mutant, an excipient and/or pharmaceutically acceptable adjuvants.

14. A method of increasing survival of an animal against infection by *Pasteurella multocida* comprising administering to the animal, an effective amount of an immunogenic composition comprising a *P. multocida* fur ompH double mutant, a *P. multocida* fur ompH galE triple mutant, an outer-membrane protein thereof prepared according to the method of claim 10.

15. A method of increasing survival of an animal against infection by *Pasteurella multocida* comprising administering to the animal, an effective amount of an immunogenic composition comprising a *P. multocida* fur ompH double mutant or an outer-member protein thereof prepared according to the method of claim 10.

16. A method of increasing survival of an animal against infection by *Pasteurella multocida* comprising administering to the animal, an effective amount of an immunogenic composition comprising a *P. multocida* fur ompH galE triple mutant or an outer-membrane protein thereof prepared according to the method of claim 10.

17. A strain of *Pasteurella multocida* deposited in the Colección Española de Cultivos Tipo (CECT) under registration number CECT 8180.

18. An immunogenic composition comprising an immunogenically effective amount of the strain of *Pasteurella multocida* of claim 17, and a pharmaceutically acceptable carrier.

19. A method of increasing survival of animals against pneumonia caused by *Pasteurella multocida* comprising administering the immunogenic composition according to claim 13 to pigs, cattle, fowl cholera, rabbits and hamsters.

* * * * *

SEQUENCE LISTING

```
<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: Fur1 primer

<400> SEQUENCE: 1 aaactttga aaaagcgc                                                   19

<210> SEQ ID NO 2
<211> LENGTH: 21
<212> TYPE: DNA
<213> ORGANISM: Artificial Sequence
<220> FEATURE:
<223> OTHER INFORMATION: Fur2

<400> SEQUENCE: 2
cttgacatta ctacatttga a                                              21

<210> SEQ ID NO 3
<211> LENGTH: 25
```

```
<212> TYPE: DNA
<213> ORGANISM: Artificial Sequence
<220> FEATURE:
<223> OTHER INFORMATION: Fur3 primer

<400> SEQUENCE: 3
cttaatagca aaataattaa ggggc                                            25

<210> SEQ ID NO 4
<211> LENGTH: 20
<212> TYPE: DNA
<213> ORGANISM: Artificial Sequence
<220> FEATURE:
<223> OTHER INFORMATION: GalEintup primer

<400> SEQUENCE: 4
gtgttgctca aatcaccggc                                                  20

<210> SEQ ID NO 5
<211> LENGTH: 20
<212> TYPE: DNA
<213> ORGANISM: Artificial Sequence
<220> FEATURE:
<223> OTHER INFORMATION: GalEintrp primer

<400> SEQUENCE: 5
ccacttggct aatataaggc                                                  20

<210> SEQ ID NO 6
<211> LENGTH: 20
<212> TYPE: DNA
<213> ORGANISM: Artificial Sequence
<220> FEATURE:
<223> OTHER INFORMATION: GalEint2up primer

<400> SEQUENCE: 6
aagccctgcc ttctatgtgg                                                  20

<210> SEQ ID NO 7
<211> LENGTH: 23
<212> TYPE: DNA
<213> ORGANISM: Artificial Sequence
<220> FEATURE:
<223> OTHER INFORMATION: Aad3 primer

<400> SEQUENCE: 7
gcccgaggca tagactgtac ccc                                              23

<210> SEQ ID NO 8
<211> LENGTH: 21
<212> TYPE: DNA
<213> ORGANISM: Artificial Sequence
<220> FEATURE:
<223> OTHER INFORMATION: pKO3-R primer

<400> SEQUENCE: 8
ttaatgcgcc gctacagggc g                                                21

<210> SEQ ID NO 9
<211> LENGTH: 20
<212> TYPE: DNA
<213> ORGANISM: Artificial Sequence
<220> FEATURE:
<223> OTHER INFORMATION: OmpH1sequp primer

<400> SEQUENCE: 9
caaacctatt ttgttttgac                                                  20
```

```
<210> SEQ ID NO 10
<211> LENGTH: 20
<212> TYPE: DNA
<213> ORGANISM: Artificial Sequence
<220> FEATURE:
<223> OTHER INFORMATION: OmpH2seqdw primer

<400> SEQUENCE: 10
caaaaacggt ggtgtcggtg                                               20

<210> SEQ ID NO 11
<211> LENGTH: 18
<212> TYPE: DNA
<213> ORGANISM: Artificial Sequence
<220> FEATURE:
<223> OTHER INFORMATION: Om21000 primer

<400> SEQUENCE: 11
catttgggca aagaagg                                                  18

<210> SEQ ID NO 12
<211> LENGTH: 20
<212> TYPE: DNA
<213> ORGANISM: Artificial Sequence
<220> FEATURE:
<223> OTHER INFORMATION: Om22000 primer

<400> SEQUENCE: 12
ctgccactgc aaaatcttgg                                               20

<210> SEQ ID NO 13
<211> LENGTH: 18
<212> TYPE: DNA
<213> ORGANISM: Artificial Sequence
<220> FEATURE:
<223> OTHER INFORMATION: RTompH1up primer

<400> SEQUENCE: 13
cgttttagta aagatgtg                                                 18

<210> SEQ ID NO 14
<211> LENGTH: 17
<212> TYPE: DNA
<213> ORGANISM: Artificial Sequence
<220> FEATURE:
<223> OTHER INFORMATION: RTompH1rp primer

<400> SEQUENCE: 14
gtcactttag attgtgc                                                  17

<210> SEQ ID NO 15
<211> LENGTH: 20
<212> TYPE: DNA
<213> ORGANISM: Artificial Sequence
<220> FEATURE:
<223> OTHER INFORMATION: RTompH2up primer

<400> SEQUENCE: 15
aaagaatatt aataacaacg                                               20

<210> SEQ ID NO 16
<211> LENGTH: 18
<212> TYPE: DNA
<213> ORGANISM: Artificial Sequence
<220> FEATURE:
<223> OTHER INFORMATION: RTompH2dw primer
```

```
<400> SEQUENCE: 16
aatcgtacta acgtcacc                                                      18

<210> SEQ ID NO 17
<211> LENGTH: 20
<212> TYPE: DNA
<213> ORGANISM: Artificial Sequence
<220> FEATURE:
<223> OTHER INFORMATION: OmpH1-2up primer

<400> SEQUENCE: 17
aatgagctga tcgctaatgc                                                    20
```